US011191909B2

(12) United States Patent
Von Hollen et al.

(10) Patent No.: US 11,191,909 B2
(45) Date of Patent: Dec. 7, 2021

(54) FEATURE ASSIGNED INHALATION AID

(71) Applicant: KONINKLIJKE PHILIPS N.V., Eindhoven (NL)

(72) Inventors: Dirk Ernest Von Hollen, Clark, NJ (US); John Nigel Pritchard, Leicester (GB)

(73) Assignee: Koninklljke Philips N.V., Eindhoven (NL)

( * ) Notice: Subject to any disclaimer, the term of this patent is extended or adjusted under 35 U.S.C. 154(b) by 616 days.

(21) Appl. No.: 15/544,098

(22) PCT Filed: Jan. 22, 2016

(86) PCT No.: PCT/EP2016/051319
§ 371 (c)(1),
(2) Date: Jul. 17, 2017

(87) PCT Pub. No.: WO2016/116591
PCT Pub. Date: Jul. 28, 2016

(65) Prior Publication Data
US 2018/0264207 A1 Sep. 20, 2018

(30) Foreign Application Priority Data
Jan. 22, 2015 (EP) .................................... 15152044

(51) Int. Cl.
*A61M 15/00* (2006.01)
*A61M 16/06* (2006.01)
(Continued)

(52) U.S. Cl.
CPC ........ *A61M 15/00* (2013.01); *A61M 15/0021* (2014.02); *A61M 15/0086* (2013.01);
(Continued)

(58) Field of Classification Search
CPC .......................... A61M 15/00; A61M 2205/60
See application file for complete search history.

(56) References Cited

U.S. PATENT DOCUMENTS

| 5,333,106 A | 7/1994 | Lanpher |
| 5,450,336 A | 9/1995 | Rubsamen |

(Continued)

FOREIGN PATENT DOCUMENTS

| EP | 1772166 A1 | 4/2007 |
| GB | 2263068 A | 7/1993 |
| WO | WO2011083377 A1 | 7/2011 |

OTHER PUBLICATIONS

Harris, D. et al., "Intelligent Inhaler", Sagentia, Cambridge, MA, Jun. 15, 2011.

*Primary Examiner* — Samchuan C Yao
*Assistant Examiner* — Nathan M Le
(74) *Attorney, Agent, or Firm* — Daniel H. Brean

(57) ABSTRACT

The present invention relates to a feedback for inhalation. In order to further improve feedback and instructions to further support the correct use of an inhaler, a feedback apparatus (10) for inhalation is provided that comprises an inhaler interface (11), a processor (14), a feedback device (16), and a feature assigner (13). The inhaler interface is configured to temporarily attach the feedback apparatus to an inhalation apparatus. The feedback device is configured to provide a feedback to the user to aid in inhalation with the inhalation apparatus. The feature assigner is configured to identify a type of a predetermined feature of the attached inhalation apparatus, and the feedback device is configured to provide the feedback in dependency of the identified type of feature to instruct the user to adjust inhalation maneuver adapted to the attached inhalation apparatus. In an example, the predetermined feature is a device type of the inhalation apparatus, and the feature assigner is configured as an inhalation (Continued)

device type assigner (70) to identify the type of a currently used inhalation device. In another example, the predetermined feature is an accessory type of the inhalation apparatus, and the feature assigner is configured as an accessory type assigner (72) to identify the type of a currently used accessory.

14 Claims, 10 Drawing Sheets

(51) Int. Cl.
*A61M 16/14* (2006.01)
*A61M 16/20* (2006.01)
(52) U.S. Cl.
CPC ............ *A61M 16/06* (2013.01); *A61M 16/14* (2013.01); *A61M 16/20* (2013.01); *A61M 2202/064* (2013.01); *A61M 2205/13* (2013.01); *A61M 2205/3331* (2013.01); *A61M 2205/3334* (2013.01); *A61M 2205/3375* (2013.01); *A61M 2205/3553* (2013.01); *A61M 2205/3592* (2013.01); *A61M 2205/52* (2013.01); *A61M 2205/581* (2013.01); *A61M 2205/582* (2013.01); *A61M 2205/583* (2013.01); *A61M 2205/60* (2013.01); *A61M 2205/6018* (2013.01); *A61M 2209/00* (2013.01); *A61M 2209/04* (2013.01)

(56) References Cited

U.S. PATENT DOCUMENTS

| | | | |
|---|---|---|---|
| 6,202,642 B1* | 3/2001 | McKinnon | A61M 15/009 128/200.14 |
| 7,343,914 B2 | 3/2008 | Abrams | |
| 9,744,319 B2 | 8/2017 | Denyer et al. | |
| 2008/0060641 A1* | 3/2008 | Smith | A61J 1/065 128/200.16 |
| 2009/0116691 A1* | 5/2009 | Scholl | G08C 17/00 382/103 |
| 2009/0120431 A1* | 5/2009 | Borgschulte | A61M 11/005 128/200.23 |
| 2011/0226242 A1* | 9/2011 | Von Hollen | A61M 15/0023 128/203.12 |
| 2011/0253139 A1* | 10/2011 | Guthrie | A61M 15/0083 128/203.14 |
| 2012/0240923 A1* | 9/2012 | Denyer | A61M 15/0086 128/202.22 |
| 2012/0266870 A1* | 10/2012 | Denyer | A61M 15/0085 128/200.14 |
| 2013/0008436 A1* | 1/2013 | Von Hollen | A61M 15/0086 128/200.14 |
| 2014/0081216 A1 | 3/2014 | Eberhart | |
| 2014/0322682 A1* | 10/2014 | Baym | G07C 9/20 434/219 |
| 2015/0283341 A1* | 10/2015 | Adams | A61M 16/0003 128/202.22 |
| 2018/0264207 A1 | 9/2018 | Von Hollen et al. | |

* cited by examiner

FEATURE ASSIGNED INHALATION AID

CROSS-REFERENCE TO RELATED APPLICATIONS

This patent application claims the priority benefit under 35 U.S.C. § 371 of international patent application no. PCT/EP2016/051319, filed Jan. 22, 2016, which claims the benefit of European Patent Application No. EP15152044.2, filed on Jan. 22, 2015, which are hereby incorporated by reference herein.

FIELD OF THE INVENTION

The present invention relates to a feedback apparatus for inhalation, to an inhaler system, and to a method for providing instructional feedback during inhalation.

BACKGROUND OF THE INVENTION

For the intake of medication, for example inhalation devices are provided. The result of a respiratory medication therapy is, among others, depending on the correct inhalation technique. For example, WO 2011/083377 A1 describes a respiratory drug delivery apparatus with a feedback and compliance device to provide feedback information to a patient regarding the use of the respiratory drug delivery apparatus. LEDs and a display are provided to give visual information such as feedback and instructions to a patient. However, it has been shown that errors in the use of the apparatus may still occur.

SUMMARY OF THE INVENTION

There may thus be a need to further improve the provision of feedback and instructions in order to further support the correct use of an inhaler.

The object of the present invention is solved by the subject-matter of the independent claims, wherein further embodiments are incorporated in the dependent claims. It should be noted that the following described aspects of the invention apply also for the feedback apparatus for inhalation, the inhaler system and the method for providing instructional feedback during inhalation.

According to a first aspect of the present invention, a feedback apparatus for inhalation is provided that comprises an inhaler interface, a processor, a feedback device and a feature assigner. The inhaler interface is configured to temporarily attach the feedback apparatus to an inhalation apparatus. The feedback device is configured to provide a feedback to the user to aid in inhalation with the inhalation apparatus. The feature assigner is configured to identify a type of a predetermined feature of the attached inhalation apparatus. The feedback device is configured to provide the feedback in dependency of the identified type of feature to instruct the user to adjust inhalation maneuver adapted to the attached inhalation apparatus. The predetermined feature comprises at least one of the group of a device type of the inhalation apparatus, an accessory type of the inhalation apparatus, and a medication type of the medication applied with the inhalation apparatus.

This provides the effect that feedback, e.g. instructions how to inhale, is provided that always apply for the particular situation. The user's comfort is thus improved, since there is no need to adapt instructions that are applicable for one type of inhaler to another type of inhaler.

The feedback apparatus is provided for the use in combination with an inhaler, e.g. an inhalation apparatus of different type. The feedback apparatus is thus a component of an inhalation kit or inhalation arrangement with a plurality of components.

The term "to identify" relates to determining or recognizing a characteristic of the inhalation apparatus. The identification can be arranged in a number of ways. The inhalation apparatus can actively provide the information to the feature assigner. The information can also be provided passively by the inhalation apparatus. For example, the feature assigner actively detects the feature or characteristic.

The identification may be provided by the inhaler interface. For example, different types of sockets and respective couplings are provided and the type of mechanical connection used determines the feature information.

As another possibility, the identification is provided via a data transmission, for example wireless communication. In an example, the data communication is provided with passive circuits, such as RFID tags.

The term "predetermined feature" relates to a certain characteristic of the inhalation apparatus that is used in combination with the feedback apparatus.

The term "assigner" relates to a unit or component of the feedback apparatus that determines the feature and assigns it to the current situation and adapts the feedback according to the feature.

The term "in dependency" relates to providing a feedback that is suitable for the current situation with respect to the identified type of the feature that has been determined as the characterizing feature, and thus prioritized to set and control the feedback that is provided to the user.

The term "inhalation maneuver" is well-known in the art and relates to inhalation and/or breath-holding techniques. Inhalation technique relates to the strength and length of a patient's inhalation and breath-holding technique relates to the duration of breath-holding. Different inhalation apparatus may require different inhalation maneuver for the efficiency of drug delivery.

According to an example, the predetermined feature is a device type of the inhalation apparatus, and the feature assigner is configured as an inhalation device type assigner provided to identify the type of a currently used inhalation device and to assign the type to a predetermined category of inhalation devices comprising at least one of the group of: a metered dose inhaler, a soft mist inhaler, a dry powder inhaler, a single breath dose nebulizer device, and another type of inhaler or nebulizer. The feedback is provided in dependency of the assigned category.

According to an example, the predetermined feature is an accessory type of the inhalation apparatus, and the feature assigner is configured as an accessory type assigner provided to identify the type of a currently used accessory and to assign the type to a predetermined category of accessories comprising at least one of the group of: valved holding chamber, intermixing mouthpiece, nose-covering mask, other types of accessory, and no accessory. The feedback is provided in dependency of the assigned accessory.

According to an example, the predetermined feature is a medication type of the medication applied with the inhalation apparatus, and the feature assigner is configured as a medication type assigner provided to identify the type of a currently used medication and to assign the type to a predetermined category of medication.

The rescue medication may also be referred to as "reliever" or bronchodilator. For example, rescue medication can be taken on an as-needed basis by the patient.

The prophylactic medication may also be referred to as "preventer", "controller", anti-inflammatory or anti-infective. For example, the prophylactic medication is supposed to be taken by patients at regular intervals in order to prevent deterioration in their condition.

In an example, if the patient or health-care professional wants to monitor adherence to treatment, then this primarily applies to the category of prophylactic medication. The rescue medication usually has no set pattern. However, over-use or sudden increase in the use of rescue medication indicates that the patient is not well controlled. It may thus be provided further an indication to the user to take their prophylactic medication, e.g. the preventer, or seek medical attention.

As an option, the inhalation device type and the accessory type are identified and assigned, and the feedback is adapted and provided accordingly. As a further option, a combination of medication identification and device or accessory type identification is provided.

According to an example, the apparatus also comprises a dispensing sensor that is configured to detect a dispensing event of the inhalation apparatus. The processor is configured to control the feedback device in dependency of a detected dispensing event.

According to an example, the feedback device provides an acoustic or visual feedback. The feedback apparatus is configured to provide the feedback as time varying set of instructions, and the time varying tactile set of instructions comprise at least a first type of feedback relating to a first action to be performed by the user, and a second type of feedback relating to a second action to be performed by the user.

According to an example, the feedback device is a vibration device and the feedback is a tactile feedback. The feedback apparatus is configured to provide the tactile feedback as a time varying tactile set of instructions. The time varying tactile set of instructions comprises at least a first type of vibration relating to a first action to be performed by the user, and a second type of vibration relating to a second action to be performed by the user.

This provides the effect that the user of an inhalation device, e.g. an inhaler of any type, is provided with instructions in a very intuitive manner. Since usually the inhalation device is arranged near the mouth or nose, the provision of visual signals may sometimes be difficult to be watched by the user. In this respect, a tactile feedback is provided in a way that does not require special attention like a focusing of the eyes in a near distance, but provides the feedback to the user over the tactile way, preferably sensed by the hand or fingers holding the apparatus.

According to an example, the feedback apparatus is configured to provide the feedback as continuous instructions for the duration of the first and the second action.

In an example, the feedback is a tactile feedback, and the feedback apparatus is configured to provide the tactile feedback as continuous instructions for the duration of the first and the second action.

In an example, the feedback device comprises a piezo vibration component.

In another example, a small electromagnetic motor is provided, with a vibrating gear mechanism. In another example, the vibration is caused by an electromagnetic actuator.

According to an example, the dispensing sensor is configured to detect a flow of a medication aerosol to be inhaled by a user and the feedback is provided upon a detected flow.

According to another example, the dispensing sensor is configured to be coupled to an outlet of a reservoir with a medication substance. The dispensing sensor detects a user-activated release of the medication substance, and the feedback is provided upon a detected release.

According to an example, the dispensing sensor is a sound or acoustic sensor that acoustically detects an inhalation by the user, and the feedback is provided upon a detected inhalation.

According to another example, the dispensing sensor is an airflow sensor that detects airflow through a predefined air-passage, which airflow is caused by an inhalation by the user. The feedback is provided upon a detected airflow.

According to an example, a patient inhalation monitoring sensor is provided that monitors a patient's inhalation maneuver or uptake of medication to provide a secondary input to the processor in addition to an input from the dispensing sensor.

For example, the patient inhalation monitoring sensor may be a flow sensor or a pressure differential sensor for monitoring e.g. airflow movement or pressure to determine a patient's inhalation maneuver or uptake of medication.

As is well-known, the term "uptake of medication" relates to the quantity of the medication that is taken by the patient.

This may provide the effect that it can be determined whether the patient's inhalation maneuver is properly done. According to an example, a proximity sensor is provided that detects the proximity to a user's mouth or another accessory, and the feedback is provided upon a detected proximity of the user's mouth.

According to an example, a data storage and/or a data transmitter is provided to store and/or to transmit data for review of sensor and operation data by a medical professional or caregiver or patient.

According to a second aspect of the present invention, an inhaler system is provided that comprises an inhalation apparatus with a reservoir with a medication substance to be administered. Further, a feedback apparatus is provided according to one of the above-mentioned examples. The feedback apparatus is temporarily attached to the inhalation apparatus. The feature assigner is configured to identify a type of a predetermined feature of the attached inhalation apparatus; and the feedback device is configured to provide the feedback in dependency of the identified type of feature to instruct the user to adjust inhalation maneuver adapted to the attached inhalation apparatus.

In an example, the dispensing sensor is configured to detect a dispensing event of the medication substance of the reservoir and the feedback is provided via a handhold (grip) portion arranged for holding the inhalation apparatus during use.

According to a third aspect of the present invention, a method for providing instructional feedback during inhalation is provided, comprising the following steps:

a) temporarily attaching feedback apparatus to an inhalation apparatus; and
b) identifying a type of a predetermined feature of the attached inhalation apparatus;
c) providing a feedback to a user to aid in inhalation with the inhalation apparatus in dependency of the identified type of feature to instruct the user to adjust inhalation maneuver adapted to the attached inhalation apparatus.

According to the present invention, the feedback apparatus senses the type of the inhalation apparatus, or the presence of any accessory to provide respectively matching inhalation instructions. The feedback apparatus thus detects the particular situation and adapts the instructions to the user accordingly. Hence, the user is always provided with optimized guidance for inhaling.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
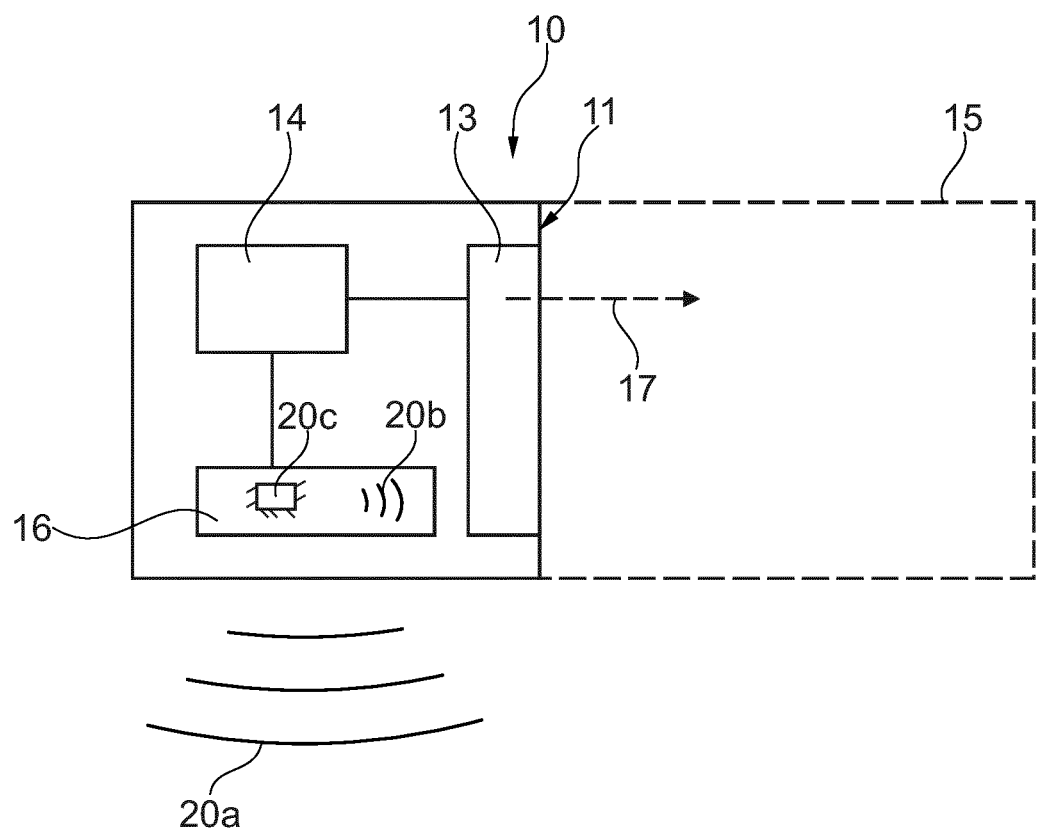
FIG. 1 shows a first example of a feedback apparatus in a schematic setup.

FIG. 1 shows a feedback apparatus 10 for inhalation. The feedback apparatus 10 comprises an inhaler interface 11, a processor 14, a feedback device 16, and a feature assigner 13. The inhaler interface 11 is configured to temporarily attach the feedback apparatus to an inhalation apparatus (indicated with dotted lines 15). The feedback device 16 is configured to provide a feedback (indicated with different examples with reference numeral "20" and an index) to the user to aid in inhalation with the inhalation apparatus. The feature assigner 13 is configured to identify a type of a predetermined feature of the attached inhalation apparatus. The identification of the type of the predetermined feature is indicated with a dotted arrow 17. The feedback device is configured to provide the feedback in dependency of the identified type of feature to instruct the user to adjust inhalation maneuver adapted to the attached inhalation apparatus.

The feedback is provided to the user in various ways. For illustration, in FIG. 1 the feedback is indicated with wave symbols 20a indicating an example, where the feedback is provided as a tactile feedback. In another example, the feedback is provided as audible signals, indicated with acoustic waves 20b, or as visible signal, indicated with a light signal 20c (see also below).

Figure 2A:
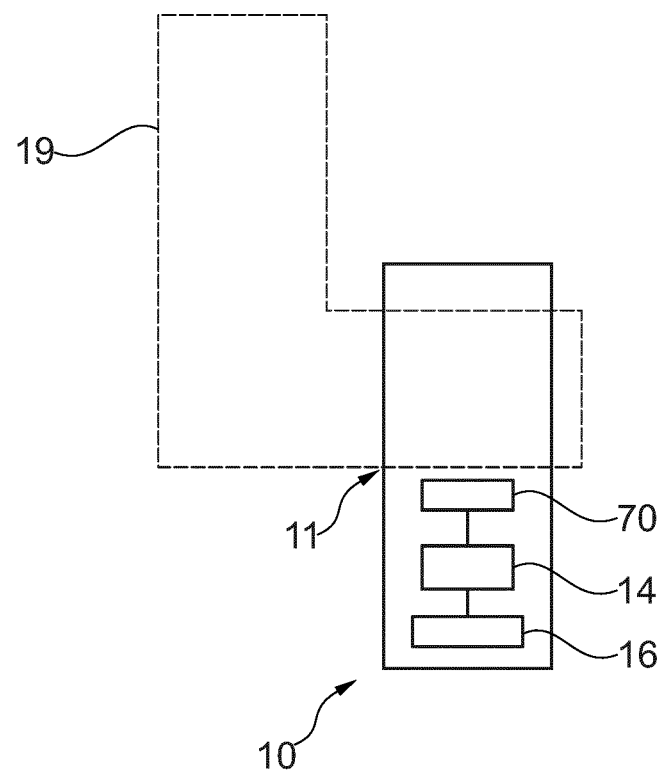
FIG. 2a shows a schematic setup of an example with an inhalation device type assigner.

As shown in FIG. 2a, in one example, the predetermined feature is a device type of the inhalation apparatus, and the feature assigner 13 is configured as an inhalation device type assigner 70 provided to identify the type of a currently used inhalation device (indicated with dotted lines 19) and to assign the type to a predetermined category of inhalation devices (see below). The feedback device 16 is configured to provide the feedback in dependency of the identified type of inhalation device.

Figure 2B:
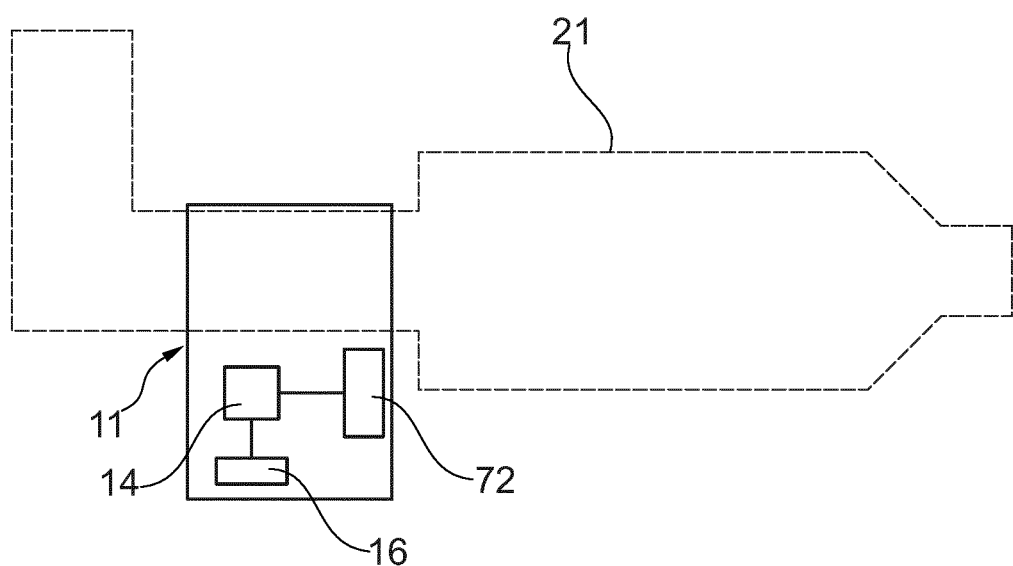
FIG. 2b shows a schematic setup of an example with an accessory type assigner.

As shown in FIG. 2b, in another example, the predetermined feature is an accessory type of the inhalation apparatus, and the feature assigner is configured as an accessory type assigner 72 provided to identify the type of a currently used accessory (indicated with dotted lines 21) and to assign the type to a predetermined category of accessories (see below). The feedback device 16 is configured to provide the feedback in dependency of the identified type of accessory.

In another example, not further shown, the feature assigner 13 is configured as a combination of the inhalation device type assigner 70 and the accessory type assigner 72. In other words, the feature assigner 13 is configured to identify the type of a currently used inhalation device and to assign the type to a predetermined category of inhalation devices, as well as to identify the type of a currently used accessory and to assign the type to a predetermined category of accessories. The feedback device 16 is configured to provide the feedback in dependency of the identified type of inhalation device and the identified type of accessory.

Figure 9:
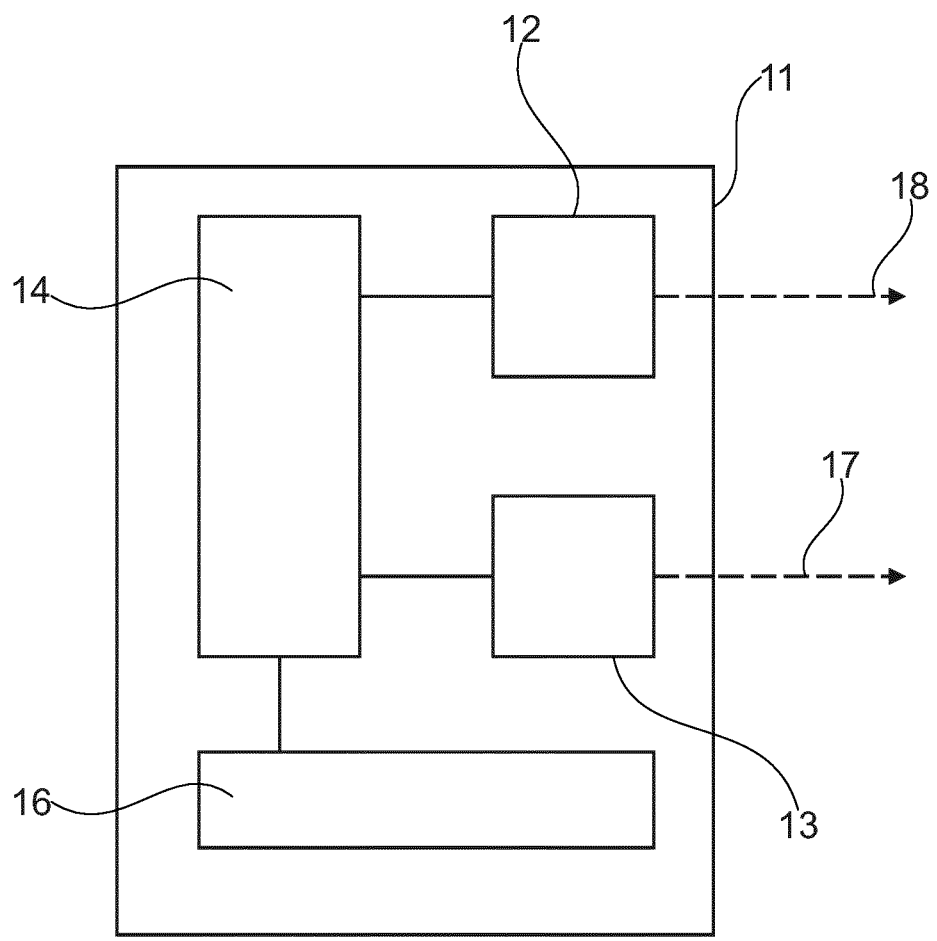
FIG. 9 shows a further example of the feedback apparatus in a schematic setup.

In an example, shown also in FIG. 9, a dispensing sensor 12 is provided. The dispensing sensor 12 is configured to detect a dispensing event of an inhalation device, which detecting of a dispensing event is indicated with a dotted arrow 18. The processor 14 is configured to also control the feedback device 16 in dependency of a detected dispensing event (see below).

As indicated above, in an example, the feedback device provides an acoustic or visual feedback. The feedback apparatus is configured to provide the feedback as time varying set of instructions; and the time varying tactile set of instructions comprise at least a first type of feedback relating to a first action to be performed by the user, and a second type of feedback relating to a second action to be performed by the user.

In an example, the feedback is a tactile feedback, indicated with vibration wave symbols 20a, and thus the feedback device 16 is a vibration device. The feedback apparatus is configured to provide the (tactile or other) feedback as a time varying tactile set of instructions. The time varying tactile instructions comprise at least a first type of vibration relating to a first action to be performed by the user, and a second type of vibration relating to a second action to be performed by the user.

In an example, a tactile coaching feedback is provided. In addition, optical feedback can be provided, such as with LEDs or the like. The inhalation device can be a manually hold inhaler, such as a pressure metered dose inhaler (PMDI) or a dry powder inhaler (DPI). The inhalation device can also be a mechanically activated inhaler, such as a soft mist nebulizer inhaler.

The metered dose inhaler relates to inhalers using a propeller gas for the outflow of a spray, i.e. an atomized spray. The soft mist inhaler relates to inhalers using a dose of atomized liquid to be mixed with a flow of air caused by inhaling. The soft mist inhaler may be provided according to the so-called Respimat® technology.

The tactile set of instructions is also referred to as tactile instructions. The first action may relate to an inhaling, i.e.

intake of breath or breathing-in, prior or post to the start of the medication dispensing and the second action may relate to a breath-holding, i.e. not breathing out again for a determined period of time.

The first type of vibration can be provided as gentle and pulsations repeated in a constant pattern for the (target-) duration of the first action that is initiated based on a sequence of dispensing events.

The second type of vibration can be provided as a differing pulsation for the (target-)duration of the second action, e.g. with a faster or slower repetition rate, or as a rhythm-like pulsations, e.g. two shorter pulses followed by a break, before being repeated.

As an option, a further, i.e. third type of vibration is provided relating to a third action, e.g. to indicate that the inhalation procedure is finished, or to indicate that a further inhalation circle should be started, i.e. a dispensing should (again) take place.

As a further option, another type of vibration is provided to indicate that an inhalation procedure can start.

According to an example, the feedback apparatus 10, i.e. the feedback device 16 is configured to provide the feedback, e.g. tactile, visual or audible feedback, as continuous instructions for the duration of the respective first and second (or more) action.

The feedback device 16 comprises a piezo vibration component in one example (not further shown in detail), or an electromagnetic actuator or drive in another example (also not shown in detail).

Turning to FIGS. 3 to 6, examples of different inhaler types are described in relation with the feedback apparatus 10.

According to an example, it is a concept to provide an inhaler interface 11 that is configured to temporarily attach the feedback apparatus to an inhalation apparatus, which may be of different type (see below). As an example, the inhaler interface 11 is provided as a receiving opening for attaching an outlet opening of a metered dose inhaler, or a soft mist inhaler, or a dry powder inhaler, or a nebulizer as mentioned above.

Figure 5:
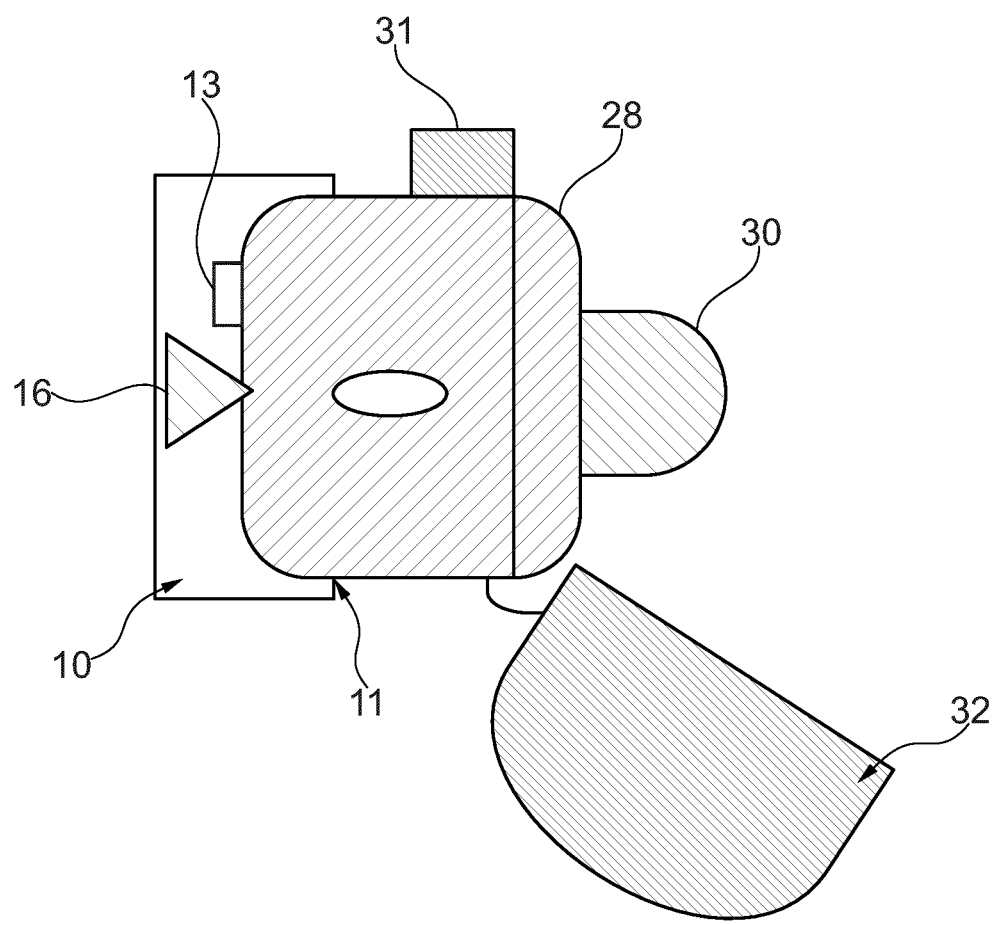
FIG. 5 shows a still further example of the feedback apparatus in combination with a dry powder inhaler capsule type.

In an example, the inhaler interface 11 is provided as a receiving opening for attaching an outlet opening of a metered dose inhaler, or a soft mist inhaler, or a dry powder inhaler, or a nebulizer. In case of a dry powder capsule type, for example as shown in FIG. 5, the inhaler interface 11 is provided as an attachment surface for attaching to a grip-portion, or interlocking on a feature of the dry powder capsule type. In another example, the feedback apparatus 10 comprises a handle or grip portion for holding the inhalation device during use.

In an example, the feedback apparatus 10 is provided as an add-on for upgrading inhalation devices of at least one of the group of: metered dose inhaler, soft mist inhaler, dry powder inhaler, and nebulizer.

Figure 3:
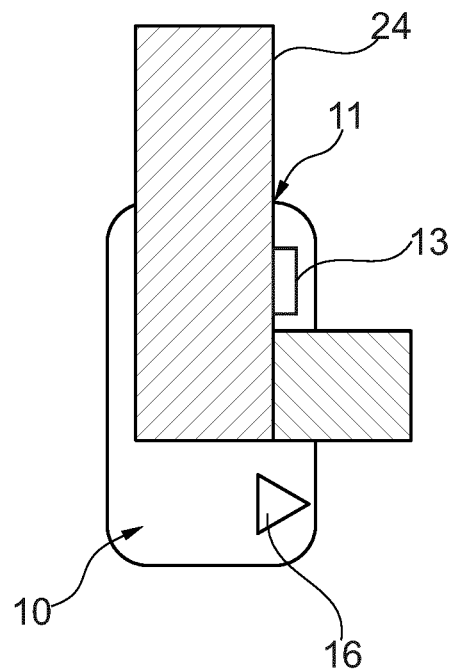
FIG. 3 shows a schematic setup of an example of the feedback apparatus of FIG. 1 in relation with an inhaler of a first type.

For example, FIG. 3 shows the feedback apparatus 10 in combination with a manually hold inhaler 24, such as a pressurized metered dose inhaler, or a dry powder inhaler.

Figure 4:
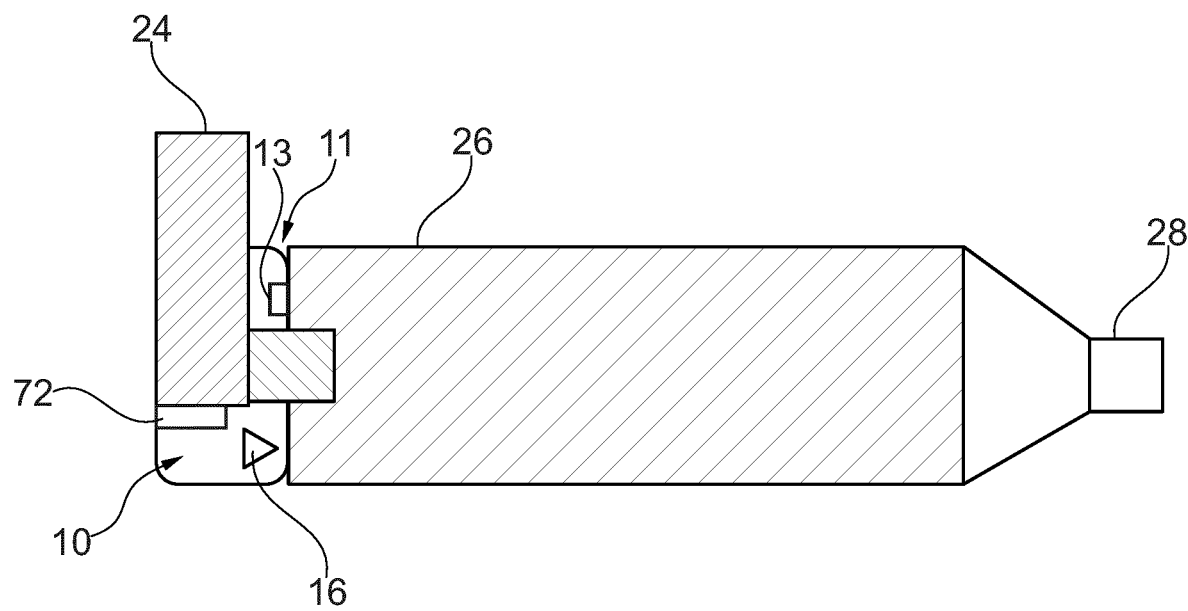
FIG. 4 shows a further example of the feedback apparatus in combination with an inhaler and a valved holding chamber or spacer.

FIG. 4 shows the feedback apparatus 10 in combination with the inhaler 24 and with a valved holding chamber 26, or spacer, having a mouthpiece 28 at the other end.

FIG. 5 shows the feedback apparatus 10 with a dry powder inhaler capsule type inhaler 28, also having a mouthpiece 30 for the inhalation by a patient. As an option, a removable cap 32 for protecting the mouthpiece 30 is shown. Further, an activation button 31 is schematically indicated.

Figure 6:
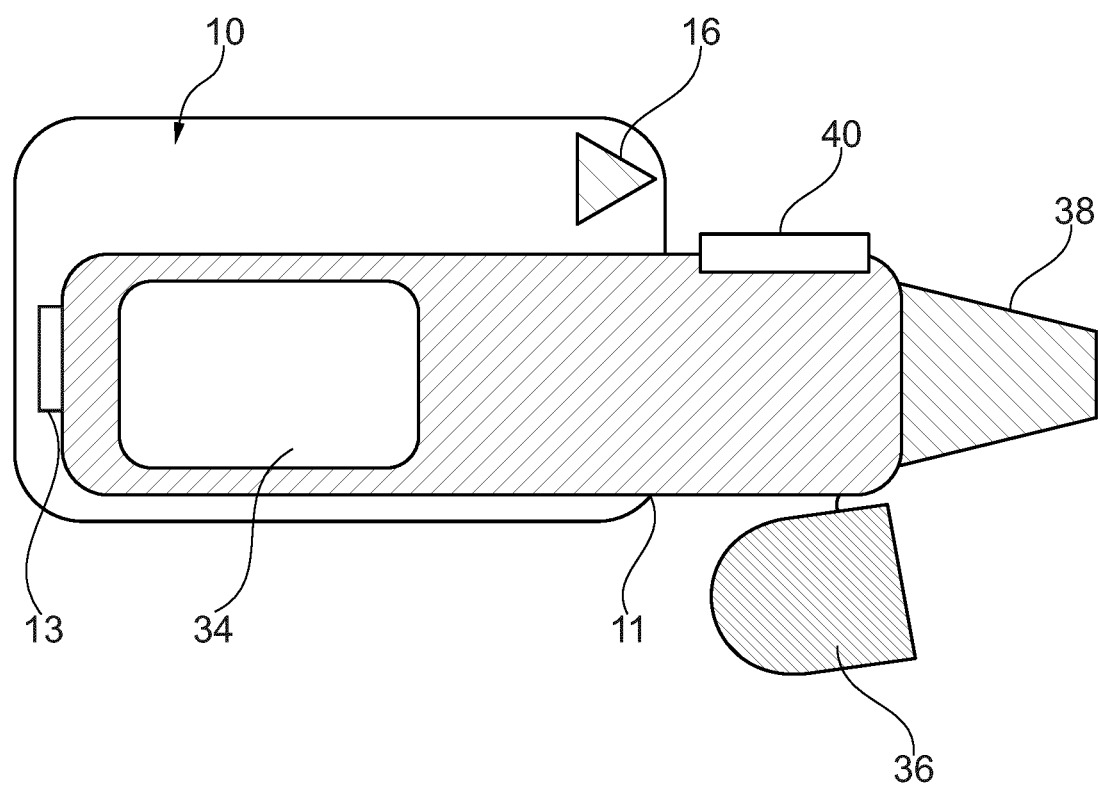
FIG. 6 shows another example of the feedback apparatus in combination with a liquid inhaler type.

FIG. 6 shows the feedback apparatus 10 in combination with a liquid inhaler type 34, for example a Respimat® inhaler. As an option, a removable protection cap 36 is shown to cover a mouthpiece 38. Still further, an activation button 40 is indicated.

With respect to the examples shown in FIGS. 3 to 6, the feedback apparatus 10 is provided as an add-on to an inhaler of different types. As a general concept for these embodiments, the feedback apparatus 10 provides the feedback in dependency of the identified type of feature, which feature is identified by the feature assigner as a type of a predetermined feature of the attached inhalation apparatus.

In an example, the feedback is provided as time varying tactile set of instructions for the correct use of the inhaler.

According to an example, the dispensing sensor 12 is configured to detect a flow of a medication aerosol to be inhaled by a user through the inhaler. The feedback is provided upon a detected flow.

The dispensing sensor 12 provides a signal when the aerosol leaves an inhalation device, according to an example. The flow of the medication can be detected by a pressure differential sensor, or by acoustic monitoring.

Figure 8:
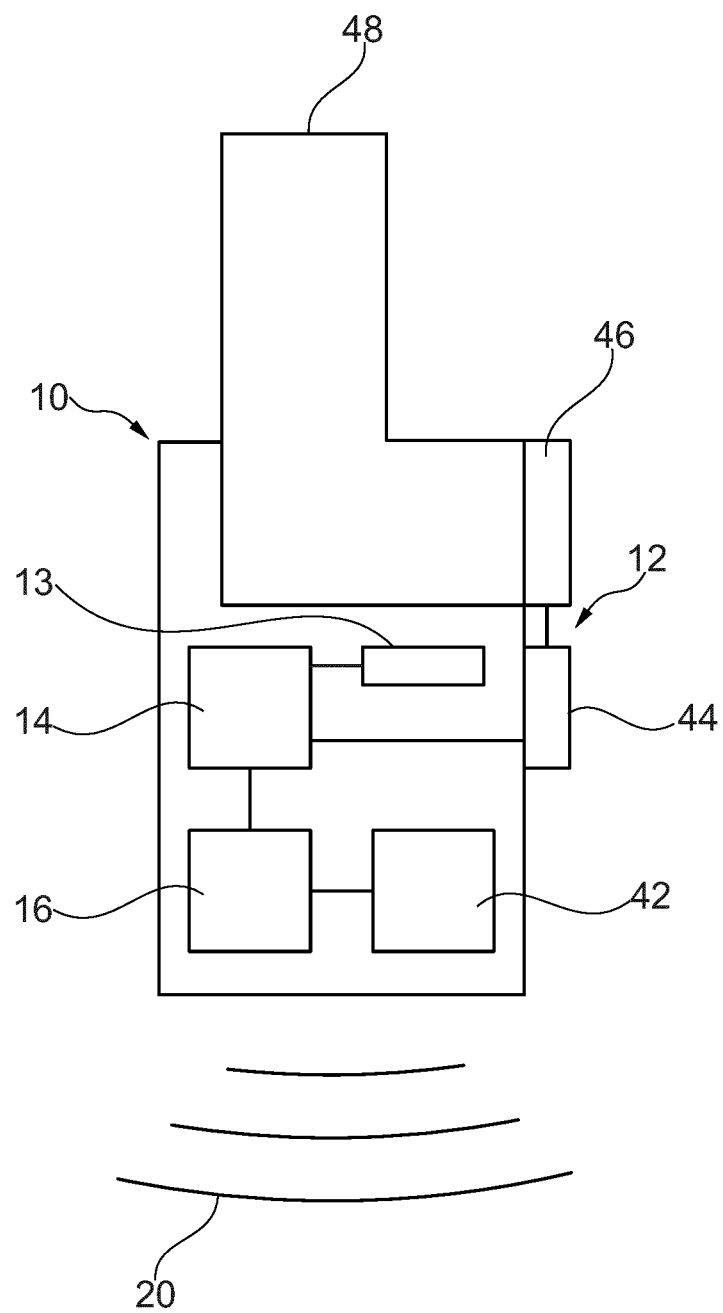
FIG. 8 shows a further example of the feedback apparatus in a schematic setup.

FIG. 8 shows an example, where the dispensing sensor 12 is a sound or acoustic sensor 42 that acoustically detects an inhalation by the user and the feedback is provided upon a detected inhalation. In an example, the sound or acoustic sensor is an MEMS microphone that is configured to detect a breathing-in of a patient.

Figure 7:
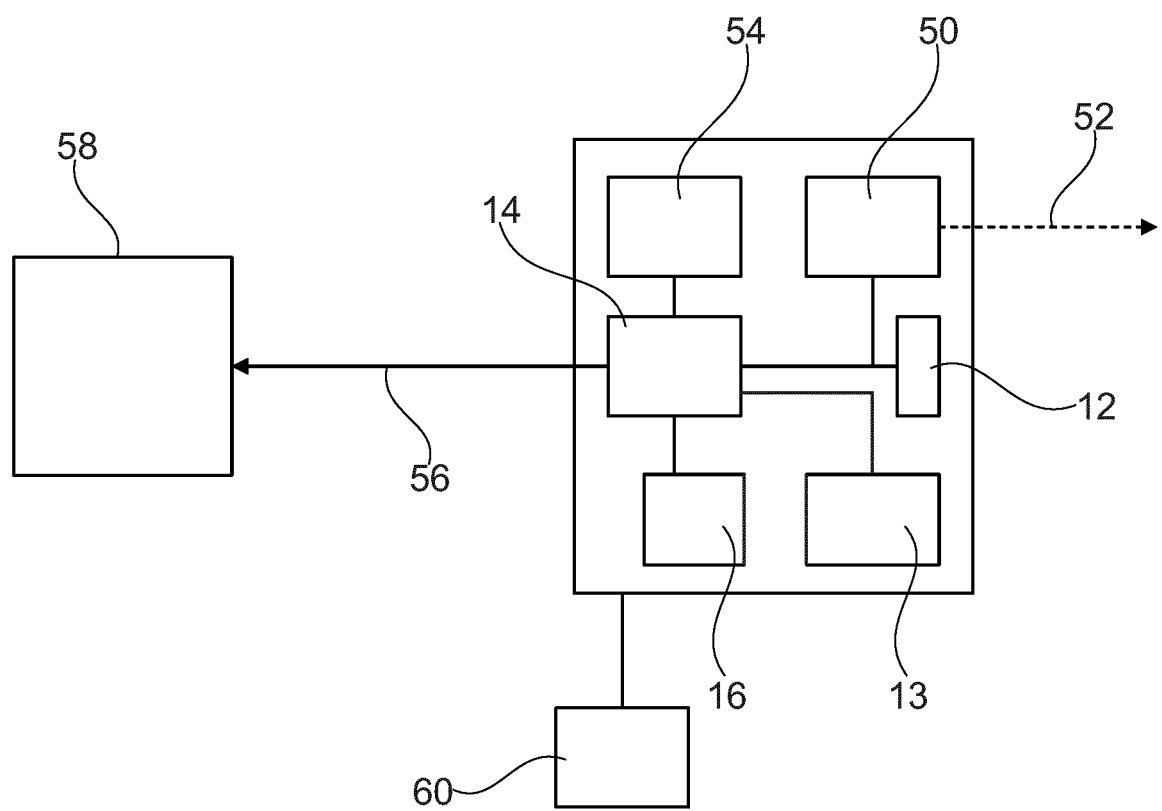
FIG. 7 shows a further example of the feedback apparatus in a schematic setup.

FIG. 7 shows a further example of the feedback apparatus 10. A patient inhalation monitoring sensor 50 is provided that monitors a patient's inhalation maneuver or uptake of medication to provide a secondary input to the processor in addition to an input from the dispensing sensor 12. A dotted arrow 52 indicates the monitoring function of the monitoring sensor 50. It is noted that the inhaler is not further shown in FIG. 7, but is provided in combination with the feedback apparatus 10.

A further option is shown in FIG. 7 in form of a data storage 54 to store data for review of sensor data and operation data. As a still further option, a data transmitter is provided, indicated with data transfer arrow 56, to transmit data for further allowing a review of the sensor and operation data by a medical professional or caregiver or patient. For example, data can be transmitted to an external data storage or workstation 58.

For example, the data storage is provided as an intermediate storage in the apparatus that is read after or during use. The data transmitter can be provided as an interface for data communication with another device during use of the feedback apparatus 10. An input interface 60 may be provided to allow an adjustment of the instructions in form of the feedback by the user in accordance with a diagnosis, therapy or treatment plan (medication plan).

It is noted that the data storage 54, the data transmitter 56 or the interface 60 are provided as options that can be provided independently of each other, or in different combinations, or combined together.

As a further example, shown as an option in FIG. 8, the dispensing sensor 12 is provided as an airflow sensor 44 that detects airflow through a predefined air passage, such as a mouthpiece 46 of an inhaler 48 schematically indicated, and the airflow is caused by an inhalation by the user and the feedback is provided upon a detected airflow.

The airflow sensor in one example uses pressure differential or thermal or ultrasonic flow sensor technology. In another example, the airflow sensor is a propeller-like arrangement provided in the air-passage. The inhalation by the user provides that the propeller-like arrangement starts to move indicating the inhalation process. Airflow movement can also be detected directly via a flow sensor or via indirect means, such as the vibration of the capsule in a dry powder inhaler.

It is noted that the dispensing sensor 12 can be a sound or acoustic sensor or an airflow sensor, or can be provided as a combination of different types of sensors.

In a further example, the dispensing sensor 12 is configured to be coupled to an outlet of a reservoir with a medication substance. The dispensing sensor detects a user-activated release of the medication substance, for example when the user activates an activation button, such as the button 31 of FIG. 5, or the button 40 of FIG. 6. The feedback is provided upon a detected release of e.g. the medication.

In an example, the dispensing sensor can be coupled to an activation interface for triggering the release of the medication substance. In one example, the apparatus is provided for a passive monitoring without interference with the actual drug delivery device. In another example, the apparatus is provided for an active feedback apparatus that besides monitoring is also provided to actively deliver medication.

Figure 10:
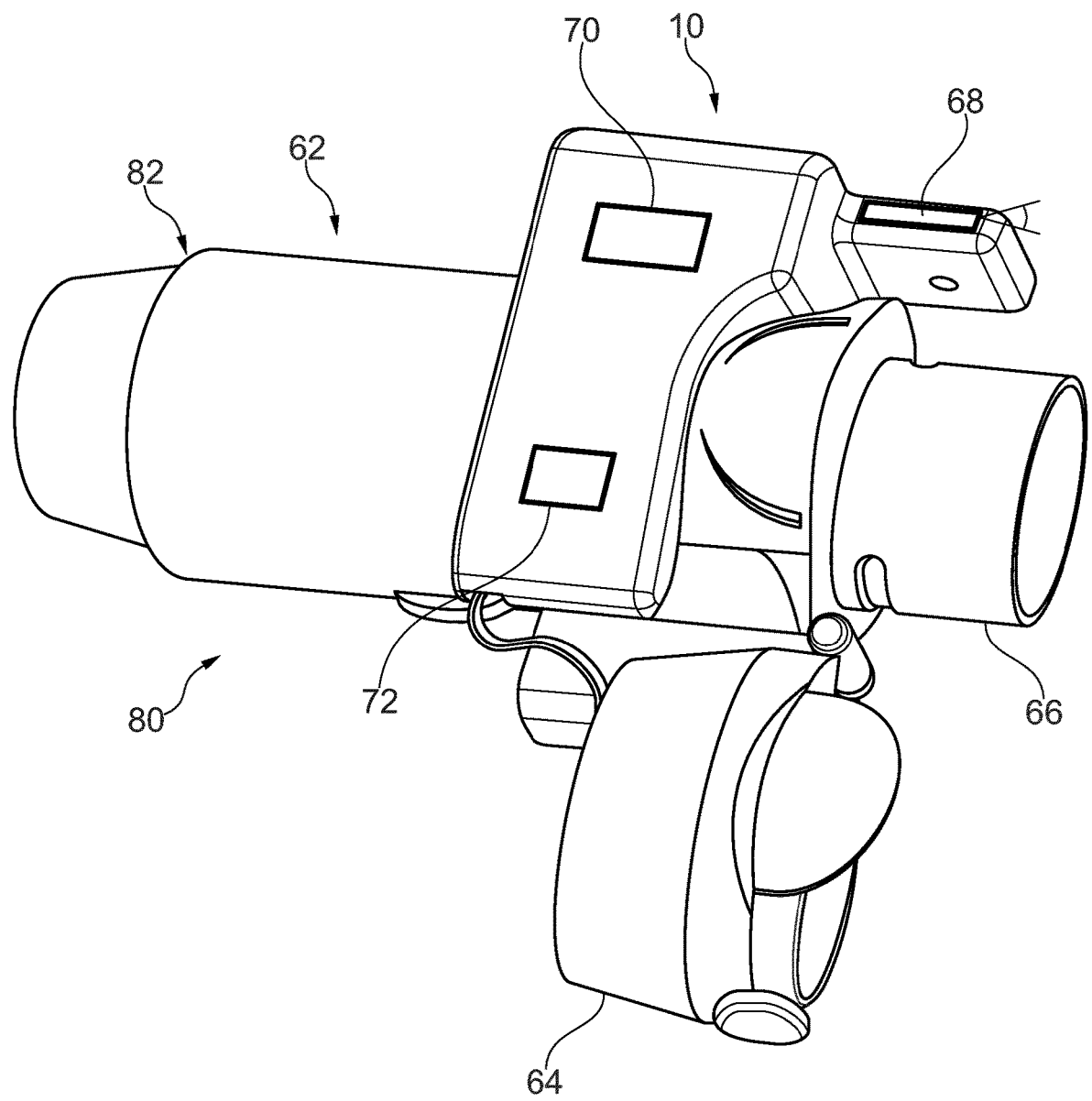
FIG. 10 shows a further example of the further feedback apparatus in combination with an inhaler forming an inhaler system.

FIG. 10 shows a perspective view of an example of the feedback apparatus 10 shown in combination with a soft mist nebulizer inhaler 62, for example a Respimat® inhaler. The soft mist nebulizer inhaler is shown with its outline or shape. For example, the feedback apparatus 10 is provided as a ring-shaped structure with one open side to insert the inhaler 62 and to attach the feedback apparatus 10 temporarily to the inhaler 62. The inhaler 62 may be provided with a protection cap 64 of a mouthpiece 66 in order to protect the latter when not in use.

The feedback apparatus 10 is provided with a proximity sensor 68 that is provided to detect the proximity to a user's mouth or another accessory and the feedback is provided upon a detected proximity to the user's mouth or other accessory. It is noted that the proximity sensor 68 is an option that is also provided for the other examples shown in the figures and mentioned in the description.

In an example, the proximity sensor is a touch sensor arranged in the vicinity of a mouthpiece such that the user touches the proximity sensor 68 when bringing the inhalation device into contact with the mouth.

The proximity sensor can also be provided as a contactless or non-contact sensor (as indicated in FIG. 10).

In an example, the feedback, e.g. a tactile feedback, is provided in a reduced or dampened manner when it is detected that an inhaler is in contact with the mouth region. When the inhaler is out of the mouth, the feedback is provided to its full extent.

Feedback can be obtained based on the change in amplitude of vibration frequency when placed in the mouth with or without an accessory such as a valved holding chamber that is used with a pressurized metered dose inhaler.

As indicated above, the feedback apparatus 10 may be provided in combination with different types of inhalers. For example, the ring-shaped structure is provided in such a manner that typically used inhalers can be inserted or attached to this region of the feedback apparatus 10 due to the nature of the inhaler usually having a mouthpiece.

As mentioned above, in a further option, also shown in FIG. 10 as an option, the predetermined feature is a device type of the inhalation apparatus, and the feature assigner is configured as the inhalation device type assigner 70 provided to identify the type of a currently used inhalation device. The inhalation device type assigner is configured to assign the type to a predetermined category of inhalation devices comprising at least one of the group of: a metered dose inhaler, a soft mist inhaler (as shown in FIG. 10 as one example), a dry powder inhaler, a single breath dose nebulizer device, and other types of inhaler. The feedback is provided in dependency of the assigned category.

Depending on the category, different typical breathing and action schemes can be identified and respective feedback schemes are predetermined and stored on the apparatus to be triggered upon identification of the currently used type of inhalation device.

The inhalation device type assigner is also referred to as inhalation device type identifier.

In an example, the feedback comprises a first type of feedback that relates to inhaling and a second type of feedback that relates to breath-holding. The duration, number and order of the different types of feedback are adapted to the detected assigned category due to the different preferred ways to use the different inhalers.

As mentioned above, in another example, turning back to FIG. 4, as an option, the predetermined feature is an accessory type of the inhalation apparatus and the accessory type assigner 72 is provided to identify the type of currently used accessory and to assign the type to a predetermined category of accessories comprising at least one of the group of: valved holding chamber (as shown in the example of FIG. 4), intermixing mouthpiece, nose-covering mask, other type of accessory, and also the category of no accessory. The feedback is provided in dependency of the assigned accessory.

As indicated, in an example, the valved holding chamber is used as an accessory for a metered dose inhaler. In another example, the intermixing mouthpiece is used as an accessory for a soft mist inhaler. In a further example, the nose-covering or nose-face covering mask is used as an accessory for a nebulizer. In a further example, no accessory is currently used, such as with a dry powder inhaler, or with a metered dose inhaler.

In a further example, the duration, number and order of the different types of feedback are also adapted to the detected accessory.

In an example, the feedback is adapted and provided in dependency of the accessory. In another example, the feedback is adapted and provided according to the inhalation device type. In a further example, both categories, i.e. the inhalation device type and the accessory type, are considered and the feedback is adapted accordingly.

As a further example, indicted in FIG. 10, an inhaler system 80 is provided. The inhaler system 80 comprises an inhalation apparatus 82, for example a soft mist inhaler, and the inhalation device comprises a reservoir with a medication substance to be administered. Further, the feedback apparatus 10 is provided according to one of the above-described examples. The feedback apparatus is temporarily attached to the inhalation apparatus. The feature assigner identifies a type of a predetermined feature of the attached inhalation apparatus, and the feedback device provides the feedback in dependency of the identified type of feature to instruct the user to adjust inhalation maneuver adapted to the attached inhalation apparatus.

In an example (not further shown), the dispensing sensor is configured to detect a dispensing event of the medication substance of the reservoir and the feedback is provided via a handhold (grip) portion arranged for holding the inhalation device during use. For example, the feedback apparatus 10 in FIG. 10 itself acts as the handhold or grip portion.

In addition to the example shown in FIG. 10, also other inhaler system types are provided, namely as inhalation systems comprising the feedback apparatus 10 and one of the inhalation device types shown in FIGS. 3 to 6, for example.

The inhaler system 80 is also referred to as inhalation system or respiratory therapy system.

In an example, an inhalation effort by the patient is detected by an inhalation sensor.

Figure 11:
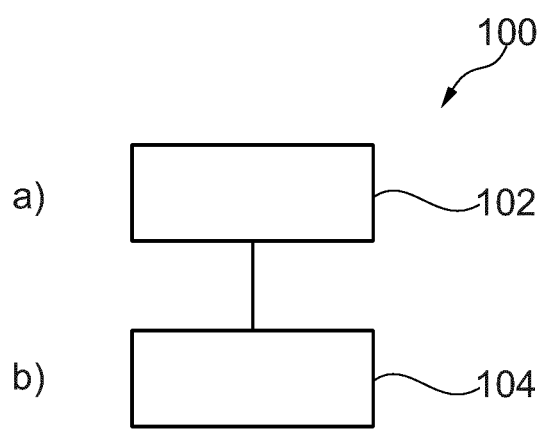
FIG. 11 shows basic steps of an example for a method for providing instructions feedback during inhalation.

FIG. 11 shows an example of a method 100 for providing instructional feedback during inhalation. The method 100 comprises the following steps: In a first step 102, also referred to as step a), a feedback apparatus is temporarily attached to an inhalation apparatus. In a second step 104, also referred to as step b), a type of a predetermined feature of the attached inhalation apparatus is identified. In a third step 106, also referred to as step c), feedback is provided to the user to aid in inhalation with the inhalation apparatus in dependency of the identified type of feature to instruct the user to adjust inhalation maneuver adapted to the attached inhalation apparatus.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A feedback apparatus for inhalation, comprising: an inhaler interface configured to temporarily attach the feedback apparatus to an inhalation apparatus; a processor; a dispensing sensor configured to detect a dispensing event of the inhalation apparatus; a feedback device configured to provide feedback to a user to aid in inhalation with the inhalation apparatus, wherein the processor is configured to control the feedback device in dependency of detection of the dispensing event by the dispensing sensor; and a feature assigner, wherein the feature assigner is an inhalation device type feature assigner configured to identify a device type of the attached inhalation apparatus and assign the identified device type to a predetermined category of inhalation devices, wherein the feedback device is configured to provide the feedback in dependency of the identified device type to instruct the user to adjust an inhalation maneuver adapted to the attached inhalation apparatus.

2. The apparatus according to claim 1, wherein the predetermined category of inhalation devices comprising a group of a metered dose inhaler, a soft mist inhaler, a dry powder inhaler, a single breath dose nebulizer device, and other types of inhaler, wherein the feedback is provided in dependency of the assigned category.

3. Apparatus according to claim 1, wherein the feature assigner is further configured as an accessory type assigner provided to identify the type of a currently used accessory and to assign the accessory type to a predetermined category of accessories comprising at least one of the group of: valved holding chamber, intermixing mouthpiece, nose-covering mask, other type of accessory, and no accessory; wherein the feedback is further provided in dependency of the assigned accessory.

4. Apparatus according to claim 1, wherein the feature assigner is further configured as a medication type assigner provided to identify the type of a currently used medication and to assign the medication type to a predetermined category of medication, comprising at least one of the group of: rescue medication and prophylactic medication.

5. The apparatus according to claim 1, wherein the feedback device provides an acoustic or visual feedback as a time varying set of instructions that comprises:
   a first type of feedback relating to a first action to be performed by the user, and
   a second type of feedback relating to a second action to be performed by the user.

6. The apparatus according to claim 1, wherein the feedback device is a vibration device, the feedback is a tactile feedback provided as a time varying tactile set of instructions comprising:
   a first type of vibration relating to a first action to be performed by the user, and
   a second type of vibration relating to a second action to be performed by the user.

7. The apparatus according to claim 5, wherein the feedback apparatus is further configured to provide the feedback as continuous instructions for the duration of the first and/or the second action.

8. The apparatus according to claim 1, wherein the dispensing sensor is further configured:
   to detect a flow of a medication aerosol to be inhaled by a user; and the feedback is provided upon a detected flow; and/or
   to be coupled to an outlet of a reservoir with a medication substance, wherein the dispensing sensor detects a user-activated release of the medication substance; and the feedback is provided upon a detected release.

9. The apparatus according to claim 1, wherein the dispensing sensor is further configured to detect an inhalation by the user, wherein the feedback is provided upon the detected inhalation.

10. The apparatus according to claim 1, further comprising:
    a patient inhalation monitoring sensor configured to monitor a patient's inhalation maneuver or uptake of medication to provide a secondary input to the processor in addition to an input from the dispensing sensor.

11. The apparatus according to claim 1, further comprising:
    a proximity sensor configured to detect the proximity to a user's mouth or another accessory, wherein the feedback is provided upon a detected proximity of the user's mouth.

12. The apparatus according to claim 1, further comprising:
a data storage and/or a data transmitter configured to store and/or to transmit data for review of sensor and operation data by a medical professional or caregiver or patient.

13. An inhaler system, comprising:
an inhalation apparatus comprising a reservoir with a medication substance to be administered;
a dispensing sensor configured to detect a dispensing event of the inhalation apparatus;
a feedback apparatus temporarily attached to the inhalation apparatus, wherein a processor is configured to control the feedback apparatus based on detection of the dispensing event by the dispensing sensor;
an inhalation device type feature assigner configured to identify a device type of the attached inhalation apparatus and assign the identified device type to a predetermined category of inhalation devices, wherein the feedback apparatus is configured to provide feedback in dependency of the identified device type to instruct the user to adjust an inhalation maneuver adapted to the attached inhalation apparatus.

14. A method for providing instructional feedback during inhalation, comprising the following steps:
a) temporarily attaching a feedback apparatus to an inhalation apparatus, wherein the feedback apparatus includes a processor;
b) detecting a dispensing event of the attached inhalation apparatus by a dispensing sensor;
c) identifying a device type of the attached inhalation apparatus and
assigning the identified device type to a predetermined category of inhalation devices by an inhalation device type feature assigner;
d) providing a feedback to a user, by the feedback apparatus, to aid in inhalation with the attached inhalation apparatus in dependency of the detecting of the dispensing event and in dependency of the identified device type to instruct the user to adjust an inhalation maneuver adapted to the attached inhalation apparatus, wherein the processor is configured to control the feedback apparatus based on the detection of the dispensing event by the dispensing sensor.

* * * * *